United States Patent
Philipp et al.

(10) Patent No.: US 7,846,373 B2
(45) Date of Patent: Dec. 7, 2010

(54) SYSTEM AND METHOD FOR TREATMENT OF WOODEN MATERIALS

(75) Inventors: Peter R. Philipp, Charlotte, NC (US); Fritz Steiner, Mellingen (CH)

(73) Assignee: Xorella AG, Wettingen (CH)

( * ) Notice: Subject to any disclaimer, the term of this patent is extended or adjusted under 35 U.S.C. 154(b) by 835 days.

(21) Appl. No.: 11/240,521

(22) Filed: Oct. 3, 2005

(65) Prior Publication Data

US 2007/0101606 A1    May 10, 2007

(51) Int. Cl.
   *B29C 35/04*    (2006.01)
(52) U.S. Cl. ............... 264/345; 264/319; 264/573; 144/380; 144/381; 34/411; 34/423
(58) Field of Classification Search ............... 264/345; 422/26, 299; 34/282, 413
See application file for complete search history.

(56) References Cited

U.S. PATENT DOCUMENTS

| | | | | |
|---|---|---|---|---|
| 1,328,660 | A | | 1/1920 | Fish |
| 4,017,980 | A | * | 4/1977 | Kleinguenther ............... 34/396 |
| 5,123,465 | A | * | 6/1992 | Gabriel ............... 144/349 |
| 5,291,757 | A | | 3/1994 | Wanger |
| 5,299,415 | A | | 4/1994 | Wanger |
| 5,447,686 | A | * | 9/1995 | Seidner ............... 422/26 |
| 5,893,216 | A | * | 4/1999 | Smith et al. ............... 34/103 |
| 6,094,840 | A | | 8/2000 | Wanger |
| 6,557,267 | B2 | | 5/2003 | Wanger |
| 6,904,903 | B1 | | 6/2005 | Vroom |
| 2001/0049884 | A1 | | 12/2001 | Wanger |
| 2003/0118471 | A1 | * | 6/2003 | Howe et al. ............... 422/26 |

FOREIGN PATENT DOCUMENTS

| | | |
|---|---|---|
| DE | 100 06 036 | 8/2000 |
| GB | 1 446 755 | 8/1976 |
| WO | WO 2006/026869 | 3/2006 |

OTHER PUBLICATIONS

Wood Products Notes by Joeph Denig, Professor and Wood Products Extension Specialist, Apr. 2002.*
Sophie Lecomte, Scrapping the barrel for recylcle, Wines & Vines by Frank Smith, Jan 2002.*

* cited by examiner

*Primary Examiner*—Monica A Huson
(74) *Attorney, Agent, or Firm*—Steptoe & Johnson LLP

(57) ABSTRACT

A method for treating a wooden material includes applying steam and vacuum to the wooden material.

12 Claims, 3 Drawing Sheets

SYSTEM AND METHOD FOR TREATMENT OF WOODEN MATERIALS

TECHNICAL FIELD

This invention relates to methods and systems for treating wooden materials.

BACKGROUND

Wooden materials, including wooden boards, crates, pallets, and dunnage, are commonly used as for transport and packaging. Wooden materials can be treated to sanitize the wood and eliminate bacteria, mold, fungi, yeast, spores, insects, and other biological organisms that may be present in the wood. Present methods of treatment, however, can consume excessive energy and also can dry the wooden materials.

SUMMARY

In general, a wooden material can be treated to sanitize and otherwise eliminate pests, including bacteria, mold, fungi, yeast, spores, insects, and other biological organisms, by heat treating the wooden material under reduced pressure.

In one aspect, a method of treating a wooden material includes applying steam and vacuum to the wooden material for an effective time period to heat the wooden material to a temperature of at least 56 degrees C. The temperature of the wooden material can be maintained at 56 degrees C. for a holding time. The holding time can be at least 30 minutes In certain circumstances, the method can include reducing pressure in a vessel containing the wooden material. In other circumstances, the method can include heating the wooden material at a first temperature for a first time period and applying steam and vacuum includes heating the wooden material at a second temperature. The first and second temperature can be substantially different. For example, the first temperature can be substantially lower than the second temperature, or the effective time period can be substantially longer than the first time period. The method can include applying an effective amount of ozone to the wooden material. The method can include heating the wooden material for a predetermined time in a vessel at a predetermined temperature. The effective time period can be at least 20 minutes and less than 240 minutes. An effective time period can also be at least 60 minutes and less than 200 minutes. In certain circumstances, the effective time period can be at least 150 minutes and less than 180 minutes. The steam can have a temperature of less than 100 degrees, and less than 90 degrees. In certain circumstances, the steam can have a temperature of greater than 60 degrees.

In another aspect, a method of manufacturing a wood treating system includes obtaining a vessel, connecting the vessel to a steam generator, and connecting the vessel to a controller configured to apply steam and vacuum to a wooden material.

In another aspect, a wood treating system includes a vessel and a controller configured to apply steam and vacuum to a wooden material.

The controller can be configured to apply steam and vacuum to a wooden material. The controller can be configured to reduce pressure in the vessel. The controller can be configured to maintain the temperature of the wooden material at 56 degrees C. for a holding time. The holding time can be at least 30 minutes. The controller can be configured to apply steam at a temperature of less than 100 degrees C., less than degrees 90 degrees C., or greater than 60 degrees C., or combinations thereof. The pressure in the system can range be at least 50 mBar and less than 700 mBar during treatment. In a vacuum, a pressure of at least 50 mBar and less than 250 mBar can be produced, and during steaming, the pressure can be at least 200 mBar and less than 700 mBar.

The wooden material can be a wooden board, wooden structure, crate, dunnage, or other wooden object.

Details are set forth in the accompanying drawings and the description below. Other features, objects, and advantages will be apparent from the description and drawings and from the claims.

DETAILED DESCRIPTION

Figure 1:
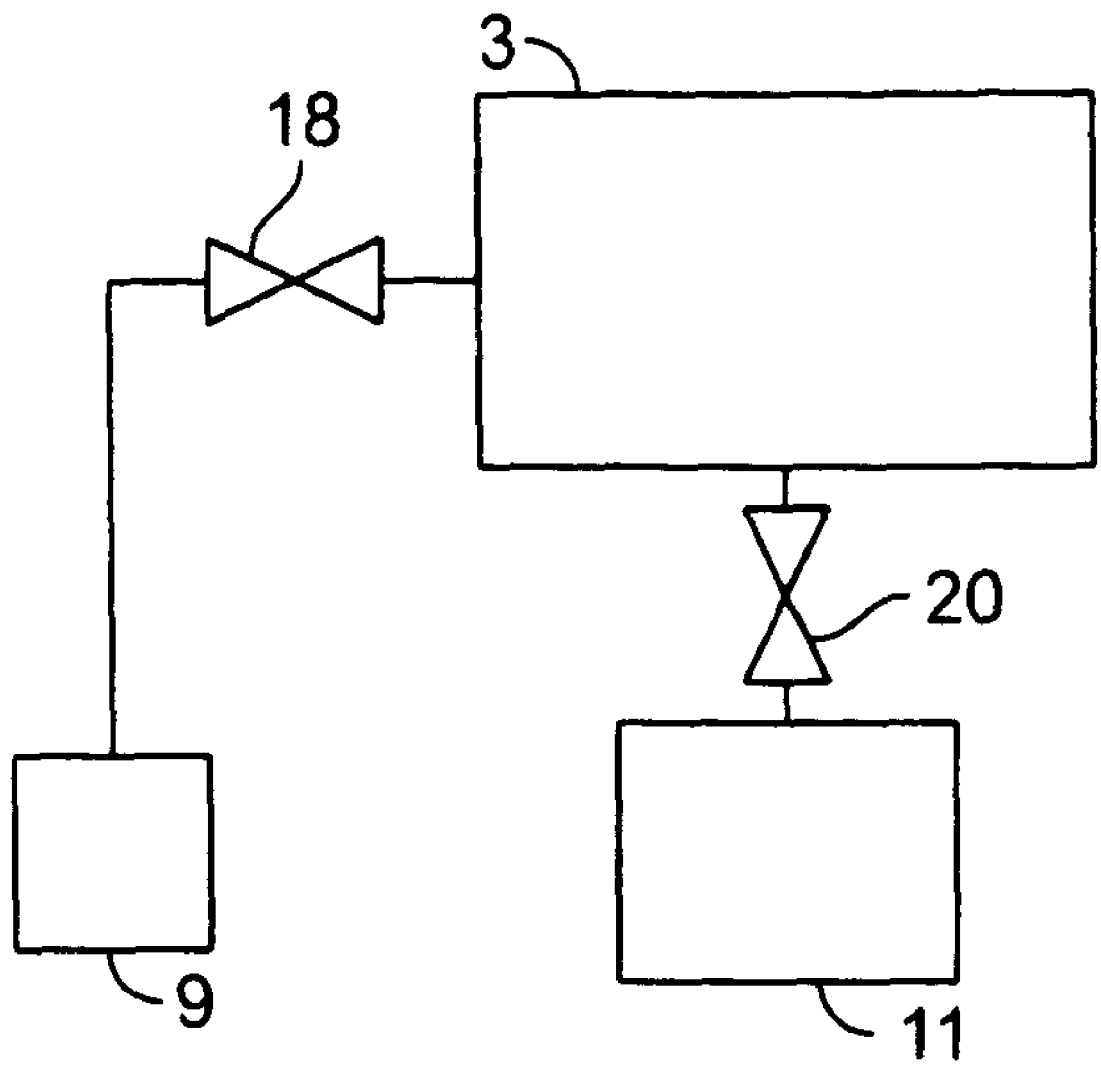
FIG. 1 is a schematic diagram depicting a wood treating system.

A method of treating wooden materials can include applying steam and vacuum to a wooden material. A wood treating system can include a vessel for containing the wood, a steam generator, and a controller configured to apply steam and vacuum to the wooden material. Applying steam and vacuum can be conducted for an effective time period so that the internal temperature of the wooden material reaches at least 56° C. The temperature can be maintained at 56 degrees C. for a holding time. The holding time can be at least 30 minutes. The heat treatment of the wooden materials can protect wooden materials prone to degradation by bacteria, mold, fungi, yeast, spores, insects, and other biological organisms. The total duration of treatment can be at least 20 minutes and less than 240 minutes. An effective time period can also be at least 60 minutes and less than 200 minutes. An effective time period can also be at least 150 minutes and less than 180 minutes. The range can include the effective time period required to heat the wooden material to 56 degrees C., and the holding time to maintain the wooden material temperature at 56 degrees C. Wooden materials can include, for example, wooden boards, wooden pallets, crates, or dunnage, such as those that can be used for trade, transport, and packaging purposes. Wooden panels, boards, crates, dunnage, or pallets are frequently chosen as packaging materials for international transit because they are more cost-effective than other non-wooden materials, even when the cost of wood treatment is considered.

The United States and the International Plant Protection Convention (IPPC) have established restrictions to stop the introduction of foreign pests due to pest outbreaks traced to transport packaging. Several countries have also established restrictions for wood packaging materials. The IPPC standard (ISPM 15) and the U.S. regulations require wood treatment by either heat treatment or fumigation with methyl bromide. Heat treatment can be preferred due to the environmental concerns caused by methyl bromide used to fumigate packaging. For heat treatment, the wooden material must be heated at the core to 56 degrees C. for 30 minutes. At present, most methods including heated air and superheated steam, tend to dry out the wood, reducing its quality, or fail to heat the core of the wooden material effectively. In addition, present methods of drying wood consume unnecessary energy because of high operating temperatures or long operating times. Thus, there is a need for an effective, energy-efficient method for treating wooden materials, particularly wooden pallets and wooden boards, to the core without overly drying the wood of diminishing its quality.

A heat treatment process for wooden materials can include subjecting a wooden material in a vessel to a reduced pressure, followed by the introduction of steam, which heats the wooden material. The interior of the vessel may ultimately reach a temperature of about 80 degrees C., which conditions and sanitizes the wooden material. Reduced pressure in the range of at least 50 mBar and less than 700 mBar can be employed. An effective time period can be at least 20 minutes and less then 240 minutes. An effective time period can also be at least 60 minutes and less than 200 minutes. In addition, an effective time period can be at least 150 minutes and less than 180 minutes.

In general, heating the wooden material can include placing the wooden material in a vessel or other container, and evacuating the vessel to a reduced pressure in the range of about 50 to 250 mBar. Steam is then introduced, and heat is allowed to permeate the wooden material for a treatment period typically between 20 and 240 minutes, during which steaming step the internal temperature of the wooden material increases to roughly between 40 and 80 degrees C. An effective time period can also be at least 60 minutes and less than 200 minutes. An effective time period can also be at least 150 minutes and less than 180 minutes. The vessel can then be evacuated, the remaining steam being simultaneously withdrawn and condensed exterior to the container. The procedure can be repeated. At the end of the treatment, the wooden material is removed. After an appropriate cool-down period, during which time a small amount of residual moisture evaporates, the wooden material can be prepared for shipment.

Each steam treatment step can be of a chosen duration, which can allows the interior of the wooden material to reach between 40 degrees and 80 degrees C., with the wooden material temperature increasing with each steaming cycle. A final interior temperature of at least 56 degrees C. ensures compliance with IPPC standards (ISPM 15) and U.S. standards. The temperature monitoring of the wooden material can be conducted using temperature sensor probes, with the treatment step time being dictated by the interior wooden material temperature desired. Alternatively, the heat transfer into the wooden material can be judged by the vessel temperature, without the need for temperature sensors. In other circumstances, the heat treatment can also for a precalculated time period, which can be found experimentally, to increase the internal temperature of the wooden material to greater than 56 degrees C., but without exceeding 60 degrees C. The calculation can result in energy conservation, and cost-saving, while still complying with ISPM standards. The vacuum employed can be at levels of between about 50 and 250 mBar, with the greatest vacuum typically being applied in the initial treatment step. Vacuums of 50, 100, 200, 500 mBar for a five cycle process can be acceptable, the vacuum serving primarily to facilitate the heat transfer between the steam and wooden material. Overall process time, including treatment steps and the time necessary to re-evacuate the chamber between treatment steps, can be in the order of 20 to 240 minutes. An effective time period can be at least 20 minutes and less than 240 minutes. An effective time period can also be at least 60 minutes and less than 200 minutes. An effective time period can also be at least 150 minutes and less than 180 minutes.

The heat treatment can be applied to the wooden material by successively increasing the temperatures of the steam phase from a first temperature for a first time period to at least one subsequent heat treatment for an effective time period. If more than one time period is involved, a steam phase temperature of at between 40 and 80 degrees can be established in a first time period and between 60 and 100 degrees C. in a further cycle for an effective time period. By increasing the holding time at a constant temperature during subsequent heat treatments, the results can also be improved.

When applying steam, the amount of water needed for wood treatment can be also reduced by an order of magnitude by re-circulation of the liquid. The heat treatment and the results achieved may be further improved in a simple manner by repeating a vacuum and steam cycle at least once.

Water or other chemicals are for wood treatment can be supplied from containers dimensioned in accordance with the volume of the liquid bath in the steamer and which, together with the steamer, form a system into which only lost liquid is fed back from outside, the lost liquid being due to the residual moisture in the steamed material and the evacuation.

The invention further provides a system for carrying out the above method, including a heated steamer connected to a water and/or chemical supply and a vacuum pump via controllers or valves. At least one container, a pump and at least two valves are provided for the liquid and/or chemical supply, the valves controlling the admission of liquid into and discharge of liquid from the steamer.

A variety of heating systems can be used. A system can be closed or open. Steam heating systems including a steam accumulator may also be used.

Applying steam at a reduced pressure can improve the heat transfer rate to the wooden material, allowing the internal temperature of the wooden material to rise relatively quickly because steam has a higher heat capacity than air. Heat transfer is theoretically complete upon reaching a temperature of 80 degrees C. Heat transfer can be accelerated by reducing pressure to approximately 100 mBar (see FIGS. 2 and 3), and then increasing the temperature as rapidly as possible to a predetermined value of approximately 80 degrees C. after reaching a 100 mBar vacuum. Since steam has a vapor saturation pressure of about 450 mBar at 80 degrees C., the pressure differential is then 450−100=350 mBar, which helps to force heat into the wooden material more efficiently and rapidly. Improved heat transfer results in a faster increase in the internal temperature of the wooden material, thereby shortening the time necessary for treating the wooden material. The reduced pressure also ensures that energy is conserved because the system can operate at a lower temperature, thereby reducing the amount of energy that would otherwise be consumed.

Referring to FIG. 1, a system for performing the wood treatment can include a vessel 3, which is configured to contain the wooden material, a vacuum pump 9, a vacuum valve 18, and a steam generator 11 with a controller 20. A steam accumulator can be used in conjunction with, or in place of, a steam generator. A steam accumulator provides a method of storing steam so that it can be released when required and thereby can decrease connecting power, fuel, and maintenance costs. The controller can include a valve. A controller can switch the vacuum valve to open, so that a vacuum can be applied to the vessel. Likewise, a steam valve can remain closed until a control unit, switches the valve to open, and steam can be introduced into the vessel.

The wooden materials can be placed in a vessel in an arrangement that maximizes exposure to the steam and vacuum treatment. For example, the wooden materials can be unrestrained. The wooden materials can also be suspended. The materials can be made to lie flat or arranged on a conveyor or rotating configuration.

The entrance of steam into the vessel can be determined by a controller device, such as valves or steam access openings, as described in U.S. Pat. No. 5,291,757, and U.S. Pat. No. 5,299,415, which are hereby incorporated by reference.

Figure 2:
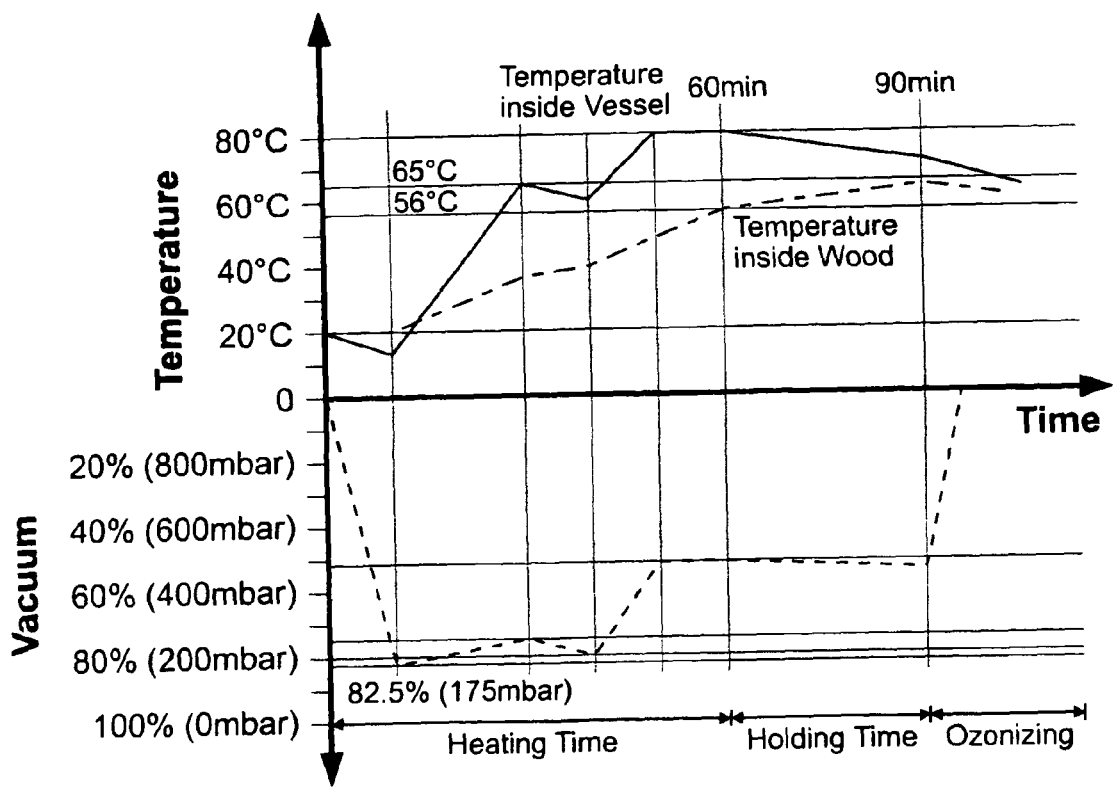
FIG. 2 is a graph depicting temperature curves during wood treatment with steam.

Referring to FIG. 2, a method of treating a wooden material can include the development of temperature (in ° C.) and pressure (in mBar) versus time (in minutes) during the treatment. In an initial phase, a first vacuum between 50 mBar and 250 mBar is produced in the vessel by opening the vacuum valve. Thereby, the initially contained air in the vessel is removed as much as possible.

In the steaming phase, one or more cycles of steaming during time can be performed. During this time, the steaming valve can be opened for flooding the vessel with steam. After reaching a defined temperature, the steam valve can be closed and the vacuum valve can be opened to reduce the pressure again to about 200 mBar or less. During the steaming periods, the pressure in the vessel can be approximately 500 mBar, and the temperature can be approximately 80° C. The pressure can be determined by the vapor pressure of water at a selected steaming temperature, which can be 80° C. Thus, in general, the steam and vacuum process, pressure can be in a range of 50 to 700 mBar. Once the steaming temperature is reached, the effective time period to heat the wooden material can range between 20 and 240 minutes. An effective time period can also be at least 60 minutes and less than 200 minutes. An effective time period can also be at least 150 minutes and less than 180 minutes. An effective time period can be the time needed to heat the core of the wooden material to at least 56 degrees C. A holding time can be the time at which a specific temperature is maintained.

The steaming cycles can be repeated as often as necessary to heat the core of the wooden materials, and the ratio of steaming duration and withdrawal of steam by vacuum can vary. The duration of a steaming cycle can be determined experimentally to bring the temperature of a wooden material to a desired temperature with minimal energy. For example, after steam is applied under reduced pressure for a defined time period, the steam can be switched off, allowing the vessel temperature to cool down to reach 60 degrees C. While the vessel temperature approaches 60 degrees C., the temperature of the wooden material either approaches or remains at 56 degrees C. By heating the wooden materials in this manner, minimal energy is used. The necessary vessel temperature and steaming duration can be calculated and applied to heat the wooden material with minimal energy. The temperature and time period can vary depending on the thermal characteristics of the system, such as insulation, time needed for establishing the reduced pressure, and rate of evaporation, for example.

Figure 3:
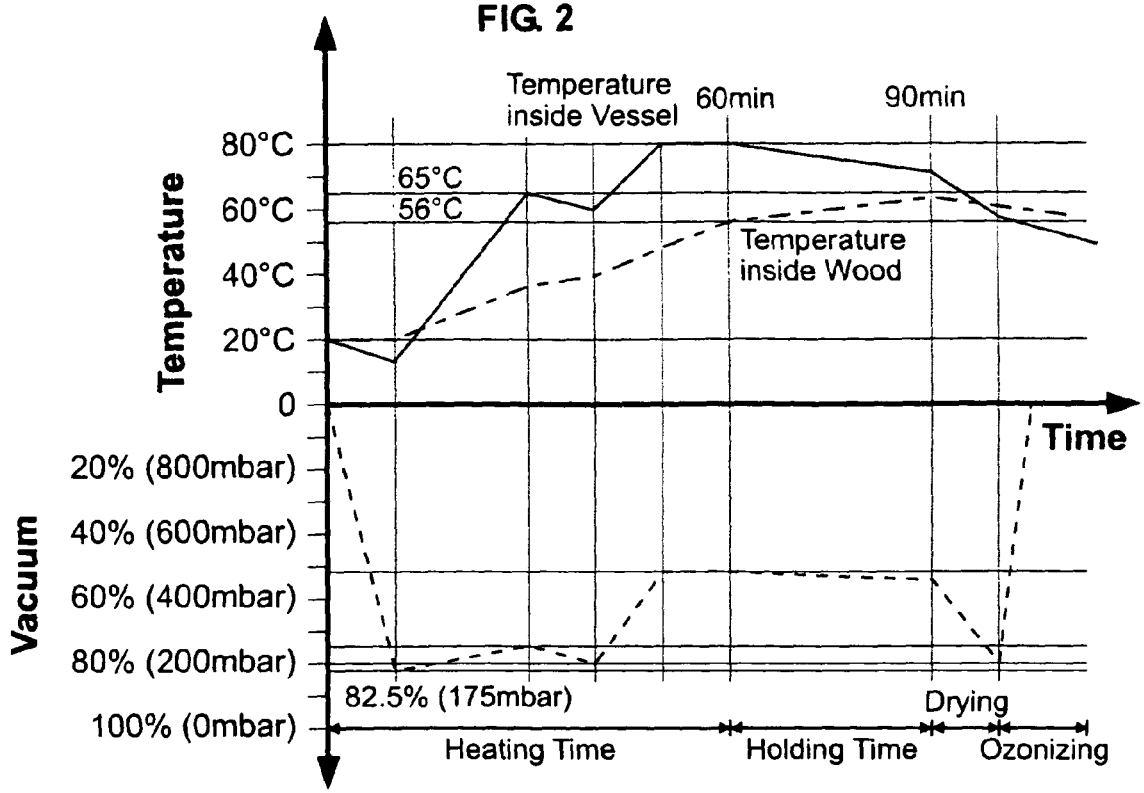
FIG. 3 is a graph depicting temperature curves during wood treatment with steam and ozone.

Referring to FIG. 3, a generalized process is shown with an optional ozonization phase. The teaming phase can be followed by an ozonization phase, which can take approximately 5 minutes and during which the pressure in the vessel can attain ambient pressure (1 Bar). The vessel can be filled with ozone-containing gas from the ozone reservoir by opening an ozone supply valve. An ozone generator can be used to supply the ozone reservoir with ozone-containing gas. An effective time period may be chosen to supply an effective amount of ozone. The time period my be chosen between about 3 minutes to about 24 hours. If ozone generators in reasonable size are not capable of furnishing the needed volumes of ozone in only a few minutes with reasonable efforts, the time between the ozonization phases can be used for filling the ozone reservoir using an ozone generator of lower output rate. As the pressure in the vessel approaches approximately 500 mBar or less, the ozone can be drawn into the wooden material. Ozone can be supplied by a gas source or an ozone generator. An ozone generator can have its own gas source, or it can use a dielectric barrier discharge. A gas source can produce a gas stream of elevated ozone concentration to the ozone reservoir. The ozone can be purged with a purging gas, and decomposed. A purging gas source can be included in the system.

Steaming cycles can also be performed after an ozonization cycle. Specifically, ozonization steps can be preceded by a reduced pressure period during which the pressure within the vessel is lowered to a pressure of at least 50 mBar and less than 700 mBar.

The ozonization phase can be followed by a purging phase. The purging valve can be opened, and a purging gas, such as purified air or oxygen, for example, can be furnished by the gas source until an ozone sensor indicates that the vessel may be safely opened. After the ozonization cycle, steam and vacuum phase can also be repeated.

Figure 4:
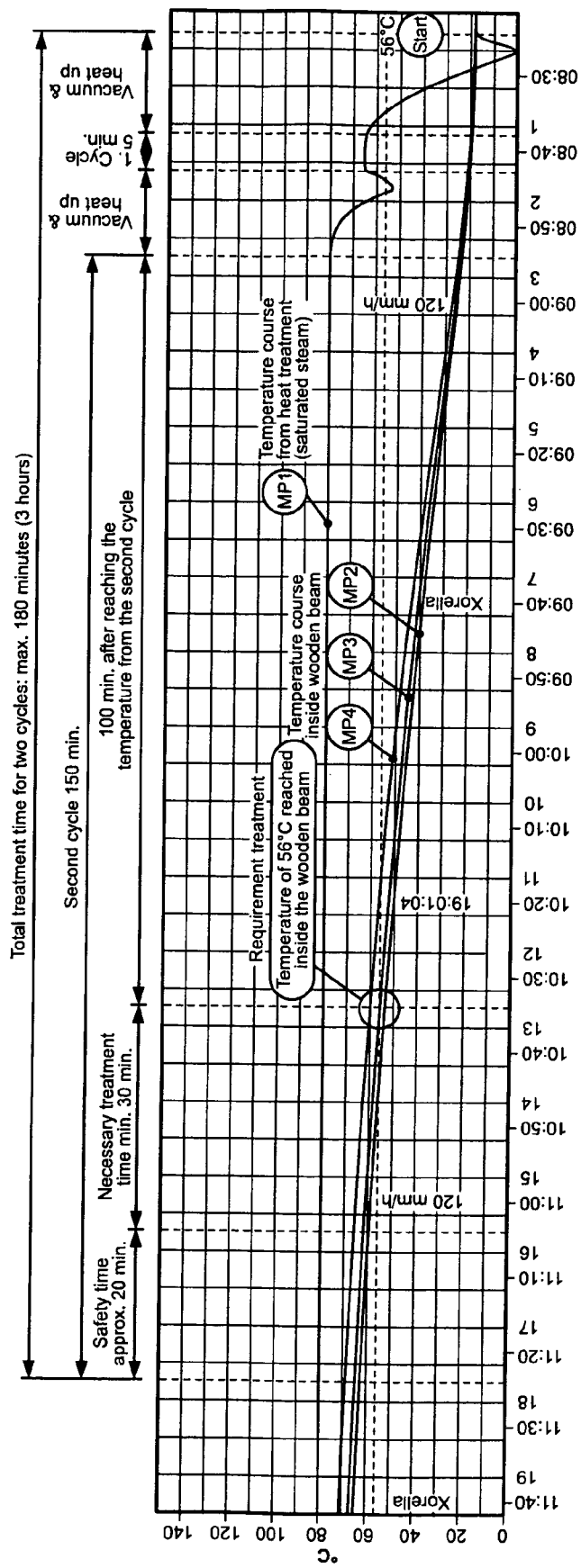
FIG. 4 is a schematic depicting temperature curves of steam and a wooden material.

Referring to FIG. 4, the graph depicts the temperature curves of temperature sensors in a wooden material plotted along with the temperature of the steam used for treatment. In this example, the steam temperature can be less than 100 degrees C. The steam temperature can also be less than 90 degrees C. The steam temperature can be greater than 60 degrees C. Applying steam and vacuum can be performed for an effective time period between 20 and 240 minutes. An effective time period can also be at least 60 minutes and less than 200 minutes. An effective time period can also be at least 150 minutes and less than 180 minutes.

Applying steam and vacuum to a wooden material accomplishes a number of surprising advantages. First, despite the relatively compact nature of wooden materials, such as wooden beams or pallets, steam accomplishes an efficient transfer of heat into the wooden material. The higher heat capacity of steam, compared that of heated air, allows for a faster and more energy efficient process of heat transfer, which provides both economic and environmental benefits. In the context of a vacuum and reduced pressure, this benefit is further emphasized because a lower temperature of steam can be used, thereby using less heat and improving energy efficiency. Generally, the duration of the steam and vacuum application can be adapted to the actual requirement, such as the kind, density and thickness of the material to be treated, for example. Applying steam at a reduced pressure can improve the heat transfer rate to the wooden material, allowing the internal temperature of the wooden material to rise relatively quickly because steam has a higher heat capacity than air. Heat transfer is theoretically complete upon reaching a temperature of 80 degrees C. Heat transfer can be accelerated by reducing pressure to approximately 100 mBar (see FIGS. 2 and 3), and then increasing the temperature as rapidly as possible to a predetermined value of approximately 80 degrees C. after reaching a 100 mBar vacuum. Since steam has a vapor saturation pressure of about 450 mBar at 80 degrees C., the pressure differential is then 450−100=350 mBar, which helps to force the energy of steam into the wooden material more efficiently and rapidly.

Applying steam and vacuum in the context of reduced pressure has the surprising advantage of sanitizing while maintaining the quality of wooden materials. For example, at a reduced pressure of at least 50 mBar and less than 700 mBar, steam temperatures of less than 100 degrees can be applied. As FIGS. 2-5 indicate, the reduced pressure of the system allows for a steam temperature of less than 100 degrees C.

within the vessel. In addition, under reduced pressure, a steam temperature of less than 90 degrees C. can also be applied. The reduced pressure also allows for a steam temperature of approximately 80 degrees C. to be applied. Surprisingly, upon placing temperature sensors in the wooden material, the internal temperature of the wooden material can be made to reach at least 56 degrees C., while the vessel temperature remained less than 100 degrees C. The reduced pressure, therefore, allows the internal temperature of the wooden material to reach at least 56 degrees C., in compliance with requirements imposed by U.S. Packaging Regulations and the ISPM phytosanitary standard, for example without exceeding 100 degrees C. As a result, the wooden material can be sanitized and treated without overly drying and diminishing the quality of the wooden material.

The wooden material can be unrestrained and subjected to reduced pressure in the vessel, such that a pressure difference is formed between the interior of the wooden material and the surrounding vessel. The pressure difference causes heat to transfer to the wooden material, driven by the pressure difference between the wooden material core and the outside of the wooden material.

The steam can have a temperature of greater than 60 degrees. The steam can also have a temperature of less than 100 degrees C. or less than 90 degrees C. The steam can also have a temperature of approximately 80 degrees C. The steam can be applied at a pressure equal to the vapor pressure of water at steaming temperature, which is about 0.5 Bar. A pressure in the range of at least 50 mBar and less than 700 mBar can also be used.

The application of steam and vacuum can allow the internal temperature of the wooden material to achieve a heated temperature of at least 56 degrees C. With sufficient treatment, the internal temperature of the wooden material can reach between 60-80 degrees. At this temperature, most biological pests, including bacteria, mold, spores, insects and fungi, can be eliminated.

The wooden material can be treated with steam and vacuum for at least one time period. One or more time periods can also be used for applying steam and vacuum to the wooden material. If more than one time period is involved, a steam phase temperature of at between 40 and 80 degrees can be established in a first time period and between 60 and 100 degrees C. in a further cycle for an effective time period.

For example, in a first time period, the wooden material can be heated at a first temperature, and at a second time period, the wooden material can be heated at a second temperature. The first and second temperatures can be substantially different.

The process of applying steam and vacuum to the wooden material can be carried out in a vessel, which can be connected to a steam generator. A steam generator can include a steamer. A steam generator can include a steam accumulator. Suitable steamers are known in the art. For example, a steamer can be designed to utilize forced recirculation, as taught in U.S. Pat. No. 6,904,903, which is hereby incorporated by reference. Steamers can include a cylindrical boiler closable by a pivotal cover. Inside the steamer, a water bath can generate steam by means of a heating device, and the appropriate heat treatment of the material introduced. In other circumstances, a vacuum can be generated to enable the heat to better access the material, such as by eliminating air pockets to ensure an optimal steam atmosphere.

A steam accumulator can be included in a wood treatment method and system. A steam accumulator provides a method of storing energy so that it can be released as steam is required and thereby can decrease connecting power, fuel, and maintenance costs.

In one example, air can be evacuated during an initial heating phase. Power, which can be applied as electrical power, can heat the water, for example to approximately 180 degrees C., at 10 bar, in a closed system of stored energy. Under reduced pressure, the water can boil, and energy is stored in the form of steam. The steam can itself drive the air out of the accumulator. A wood treating system can include a controller. The controller can include a deculator. A deculator can be provided to force out any air in the steam accumulator. The deculator can include a valve, which is configured to open so long as air is being forced out of the accumulator, and close when only steam remains. The deculator can be configured to be leakproof.

In another example, a vacuum can be applied to remove any remaining air in the accumulator. A controller can ensure that the vessel does not open or leak during a steaming or vacuuming phase.

A steam accumulator can be used in place of, or in conjunction with a water bath. A steam accumulator provides a method of storing energy so that it can be released as steam when required and thereby can decrease connecting power, fuel, and maintenance costs. Steam accumulation is the process of storing surplus energy produced at times of low demand for subsequent release to meet the consumer requirements at times of high demand. When steam demand from a system is low, and the accumulator is capable of generating more steam than is required, the surplus energy can emit a mass of water stored under pressure, resulting in energy transfer. The stored water can increase in temperature until it finally achieves the saturation temperature for the pressure at which the accumulator is operating. The vessel can be configured to have a steady supply of saturated steam. The greater the drop in pressure, the smaller the vessel required, which can decrease the system cost while providing a greater storage capacity. The steam accumulator can be applied at various temperatures. For example, the steam accumulator can be heated to 180 degrees C. at 10 bar before the wooden material is heated. When the wooden material is heated, the temperature and pressure in the vessel can be reduced to 80 degrees C. and 470 mBar. The difference in enthalpy can promote heat transfer into the wooden material. Various sizes and designs of steam accumulators ensure that a desired flow rate is achieved. Steam accumulators are available, for example, from David Oakland Associates in the United Kingdom.

In one example, the steamer can be charged with the material to be treated. In the next step, a vacuum pump can be switched on until a vacuum of at least 100 mBar has been generated in the steamer. The pump can then be shut off. A feed valve for water or a chemical supply can then be opened and a predetermined volume of liquid is admitted into the steamer to form a liquid bath. The liquid bath and the steam phase can be formed are heated to a pre-determined temperature. After the wooden material to be treated has been held for a pre-determined time in the saturated steam phase the liquid is pumped out of the steamer into a container. The vacuum pump can then be reactivated. After a pre-selected evacuation, cooling and drying period, the vacuum pump can switched off and ambient air can be admitted into the steamer, and the wooden material can be removed.

An effective time period for treatment can be at least 20 minutes and less than 240 minutes, to allow the wooden material to reach a temperature of at least 56 degrees C. An effective time period can also be at least 60 minutes and less than 200 minutes. An effective time period can also be at least 150 minutes and less than 180 minutes. Once heated, the temperature of the wooden material can be maintained at approximately 56 degrees C. for a holding time. The holding time can be at least 30 minutes. During the effective time period and the holding time, bacteria, mold, fungi, yeast, spores, insects, and other biological organisms can be eliminated. Optionally, the wooden materials can be subjected to ozone treatment. An effective time period may be chosen to supply an effective amount of ozone. The time period my be chosen between about 3 minutes to about 24 hours. The steps can be repeated for additional treatment phases and cycles, depending on the desired result. For example, an additional steaming period can be performed to reduce air quantity in the vessel. Repeated cycles of steaming of textile materials are described in U.S. Pat. Nos. 6,557,267 and 6,094,840, which are hereby incorporated by reference.

Other embodiments are within the scope of the following claims.

What is claimed is:

1. A method of treating a wooden material comprising applying steam and vacuum heating the wooden material at a first temperature for a first time period, and applying steam and vacuum to the wooden material for an effective time period to heat the wooden material to a second temperature of at least 56 degrees C., wherein the first temperature and second temperature are substantially different.

2. The method of claim 1, wherein applying steam includes reducing pressure in a vessel containing the wooden material.

3. The method of claim 1, wherein the wooden material is a wooden board, crate, pallet, or dunnage.

4. The method of claim 1, further comprising heating the wooden material for a predetermined time in a vessel at a predetermined temperature.

5. The method of claim 1, wherein the temperature of the wooden material is maintained at 56 degrees C. for a holding time.

6. The method of claim 5, wherein the holding time is at least 30 minutes.

7. The method of claim 1, where in the steam has a temperature of less than 100 degrees C.

8. The method of claim 1, wherein the steam has a temperature of less than 90 degrees C.

9. The method of claim 8, wherein the steam has a temperature of greater than 60 degrees C.

10. The method of claim 1, wherein the first temperature is substantially lower than the second temperature.

11. The method of claim 1, wherein the effective time period is substantially longer time than the first time period.

12. The method of claim 1, further comprising applying an effective amount of ozone to the wooden material.

* * * * *